US007278992B2

United States Patent
Cropper et al.

(10) Patent No.: US 7,278,992 B2
(45) Date of Patent: Oct. 9, 2007

(54) MEDICAL INSTRUMENT HAVING MEDICAL-TREATMENT ELECTRODE

(75) Inventors: Michael S. Cropper, Edgewood, KY (US); Patrick Weizman, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 242 days.

(21) Appl. No.: 11/047,934

(22) Filed: Feb. 1, 2005

(65) Prior Publication Data

US 2006/0173402 A1 Aug. 3, 2006

(51) Int. Cl.
*A61B 18/18* (2006.01)

(52) U.S. Cl. .......................... 606/41; 606/40; 606/46; 128/898

(58) Field of Classification Search .................. 606/41, 606/46–50, 40, 44; 607/101, 102; 128/898; 600/127, 129
See application file for complete search history.

(56) References Cited

U.S. PATENT DOCUMENTS

| | | | | |
|---|---|---|---|---|
| 5,228,451 A * | 7/1993 | Bales et al. | ............... | 600/564 |
| 5,336,222 A * | 8/1994 | Durgin et al. | ............... | 606/50 |
| 5,360,428 A * | 11/1994 | Hutchinson, Jr. | ............ | 606/45 |
| 5,403,311 A * | 4/1995 | Abele et al. | .................. | 606/49 |
| 5,482,054 A * | 1/1996 | Slater et al. | ................ | 600/564 |
| 5,496,317 A * | 3/1996 | Goble et al. | .................. | 606/48 |
| 5,599,346 A * | 2/1997 | Edwards et al. | .............. | 606/41 |
| 5,702,390 A * | 12/1997 | Austin et al. | ................. | 606/48 |
| 5,849,011 A * | 12/1998 | Jones et al. | .................... | 606/47 |
| 5,957,863 A * | 9/1999 | Koblish et al. | ............. | 600/567 |
| 5,964,727 A * | 10/1999 | Edwards et al. | ............. | 604/22 |
| 6,096,037 A * | 8/2000 | Mulier et al. | ................. | 606/49 |
| 6,802,840 B2 * | 10/2004 | Chin et al. | .................... | 606/41 |
| 6,808,491 B2 * | 10/2004 | Kortenbach et al. | ........ | 600/104 |
| 6,837,884 B2 * | 1/2005 | Woloszko | .................... | 606/32 |
| 2001/0009985 A1* | 7/2001 | Durgin et al. | ................ | 604/22 |
| 2002/0072740 A1* | 6/2002 | Chandrasekaran et al. | .... | 606/41 |
| 2002/0078967 A1* | 6/2002 | Sixto et al. | ................. | 128/898 |
| 2002/0099369 A1* | 7/2002 | Schulze | ....................... | 606/50 |
| 2002/0147447 A1* | 10/2002 | Long | .......................... | 606/41 |
| 2003/0014010 A1* | 1/2003 | Carpenter et al. | .......... | 604/117 |
| 2004/0215188 A1* | 10/2004 | Mulier et al. | ................. | 606/51 |
| 2005/0113760 A1* | 5/2005 | Chachques et al. | ......... | 604/174 |
| 2005/0209564 A1* | 9/2005 | Bonner et al. | .............. | 604/173 |

* cited by examiner

*Primary Examiner*—Michael Peffley
*Assistant Examiner*—Victoria Chen
(74) *Attorney, Agent, or Firm*—Victor Moreno

(57) ABSTRACT

A first medical instrument includes a medical catheter, a rotatable member, an injection needle, and at least one medical-treatment electrode supported by the rotatable member. The medical catheter has a distal end. The rotatable member is connected to the medical catheter and is rotatable with respect to the medical catheter. The injection needle is movable to extend from, and to retract within, the distal end of the medical catheter. A second endoscope adjunct includes a medical catheter, a rotatable member, and at least one medical-treatment electrode supported by the rotatable member. The medical catheter has a distal end and has a lumen adapted to receive the injection needle. The rotatable member is connected to the medical catheter is rotatable with respect to the medical catheter.

16 Claims, 5 Drawing Sheets

US 7,278,992 B2

MEDICAL INSTRUMENT HAVING MEDICAL-TREATMENT ELECTRODE

FIELD OF THE INVENTION

The present invention is related generally to medical systems, and more particularly to a medical instrument having a medical-treatment electrode.

BACKGROUND OF THE INVENTION

A known medical instrument includes a catheter having a distal end insertable into a working channel opening of a flexible endoscope. The distal end of the catheter has two medical-treatment electrodes which act as a hemostat to stop bleeding in esophageal tissue of a patient. An injection needle is provided and, when needed, extends from a lumen in the distal end of the catheter to deliver a vasoconstrictor drug to help control hemorrhaging before using a medical radio-frequency (RF) generator to activate the electrodes.

Still, scientists and engineers continue to seek improved medical instruments having a medical-treatment electrode.

SUMMARY

A first embodiment of a medical instrument of the invention includes a medical catheter, a rotatable member, an injection needle, and at least one medical-treatment electrode. The medical catheter has a distal end. The rotatable member is connected to the medical catheter proximate the distal end of the medical catheter and is rotatable with respect to the medical catheter between a first rotational position and a second rotational position. The injection needle is movable to extend from, and to retract within, the distal end of the medical catheter for at least one of the first and second rotational positions of the rotatable member. The at-least-one medical-treatment electrode is supported by the rotatable member.

A second embodiment of a medical instrument of the invention includes a medical catheter, a rotatable member, and at least one medical-treatment electrode. The medical catheter has a distal end and has a lumen adapted to receive an injection needle movable in the lumen to extend from, and to retract within, the distal end of the medical catheter. The rotatable member is connected to the medical catheter proximate the distal end of the medical catheter and is rotatable with respect to the medical catheter between a first rotational position and a second rotational position. The at-least-one medical-treatment electrode is supported by the rotatable member.

Several benefits and advantages are obtained from one or more of the embodiments of the invention. In one application, having a rotatable member support the at-least-one medical-treatment electrode allows the medical catheter to be inserted into, and withdrawn from, the esophagus (or other body lumen) of a patient with the rotatable member rotated to extend straight out or straight back (retroflexed) from the distal end of the medical catheter and allows the rotatable member to rotate to an advantageous rotational position to provide more intimate contact between the at-least-one medical-treatment electrode and patient esophageal (or other) tissue for improved hemostasis.

DETAILED DESCRIPTION

Figure 1:
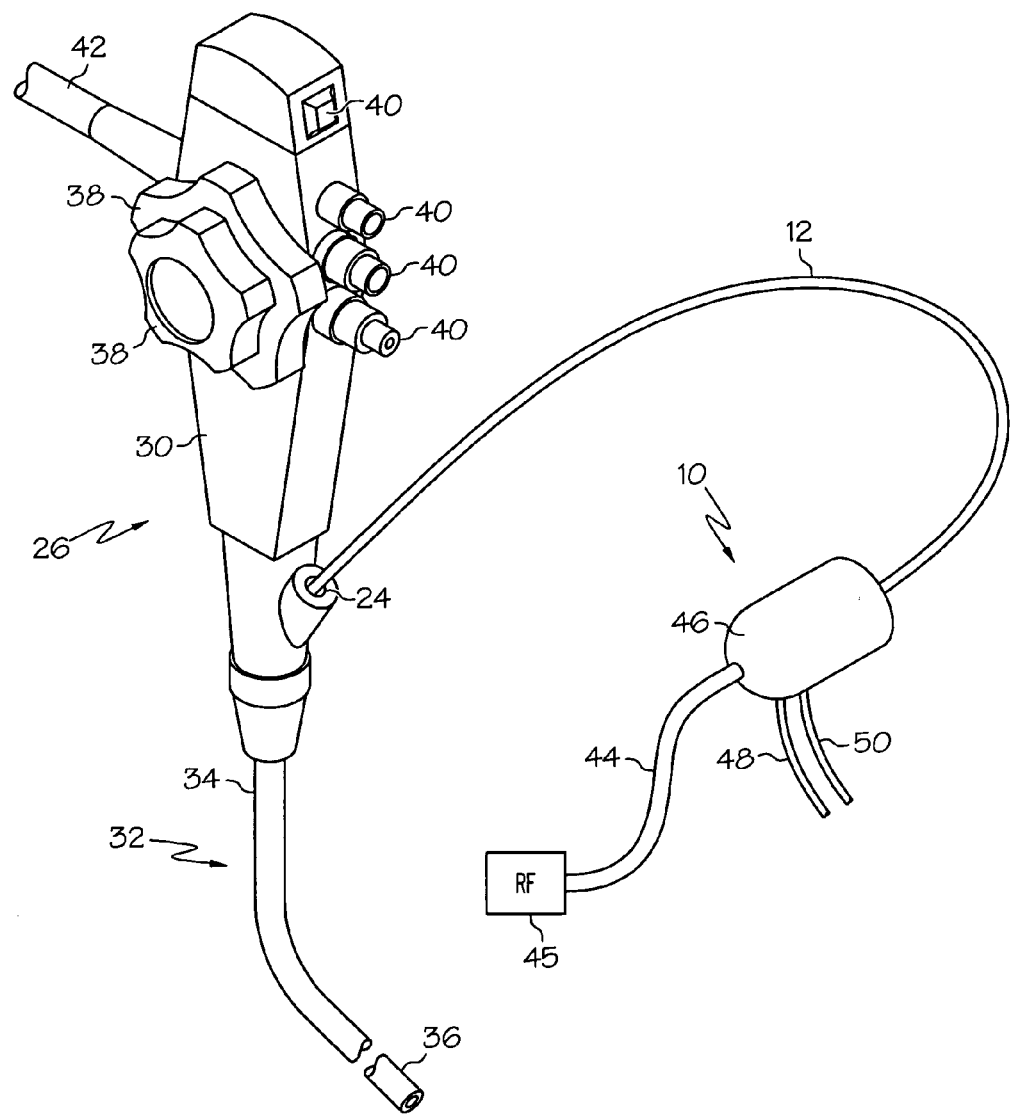
FIG. 1 is a schematic, perspective view of a first embodiment of a medical instrument of the invention and of an embodiment of a flexible endoscope and a medical radio-frequency (RF) generator which, in one employment, are used with the medical instrument, wherein the distal portion of the catheter of the medical instrument has been inserted into a working channel opening of the endoscope.

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, examples, etc. can be combined with any one or more of the other following-described embodiments, examples, etc.

A first embodiment of a medical instrument 10 of the invention is shown in FIGS. 1-7 and includes a medical catheter 12, a rotatable member 14, an injection needle 16, and at least one medical-treatment electrode 18 and 20. The medical catheter 12 has a distal end 22. The rotatable member 14 is connected to the medical catheter 12 proximate the distal end 22 of the medical catheter 12 and is rotatable with respect to the medical catheter 12 between a first rotational position and a second rotational position. The injection needle 16 is movable to extend from, and to retract within, the distal end 22 of the medical catheter 12 for at least one of the first and second rotational positions of the rotatable member 14. The at-least-one medical-treatment electrode 18 and 20 is supported by the rotatable member 14.

In one enablement of the embodiment of FIGS. 1-7, the distal end 22 of the medical catheter 12 is insertable into a working channel opening 24 of an endoscope 26. In another enablement, the distal end 22 of the medical catheter 12 is insertable into a channel (not shown) on the outside of the flexible tube 32 of the endoscope 26 or is attachable to a ring (not shown) on the outside of the distal end portion 36 of the flexible tube 32 of the endoscope 26. In another enablement, the distal end 22 of the medical catheter 12 is insertable into a channel of a steerable medical device (not shown). Other enablements (including the use of the medical catheter 12 without channel or ring assistance) are left to the artisan.

Figure 2:
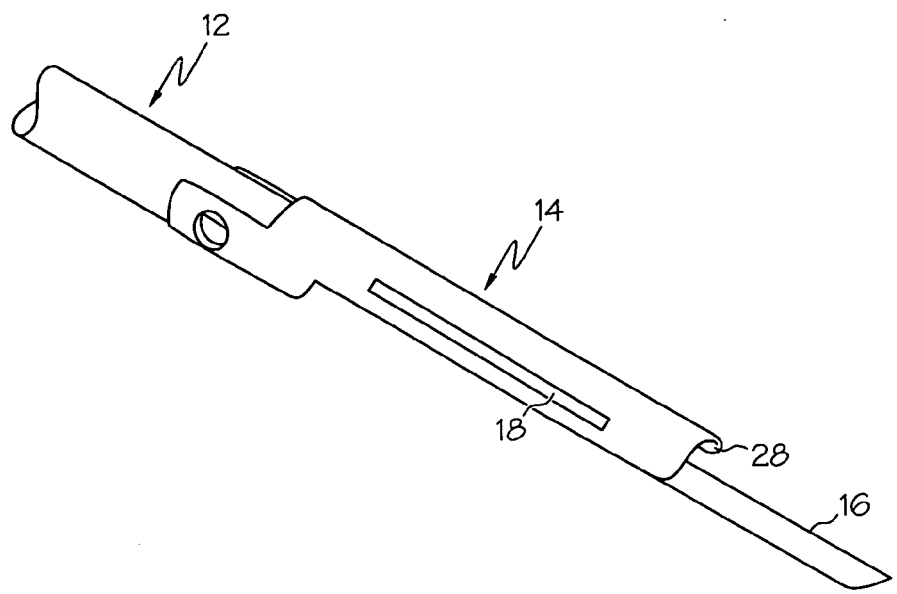
FIG. 2 is a perspective view of an assemblage of the injection needle, the rotatable member, and the distal portion of the catheter of the medical instrument of FIG. 1, wherein the rotatable member has been rotated to a first rotational position.
Figure 3:
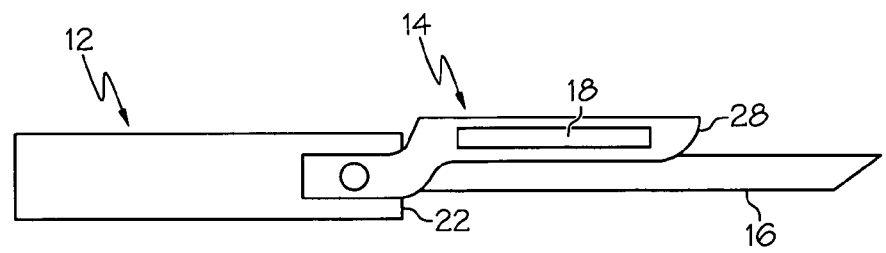
FIG. 3 is a side elevational view of the assemblage of FIG. 2.
Figure 4:
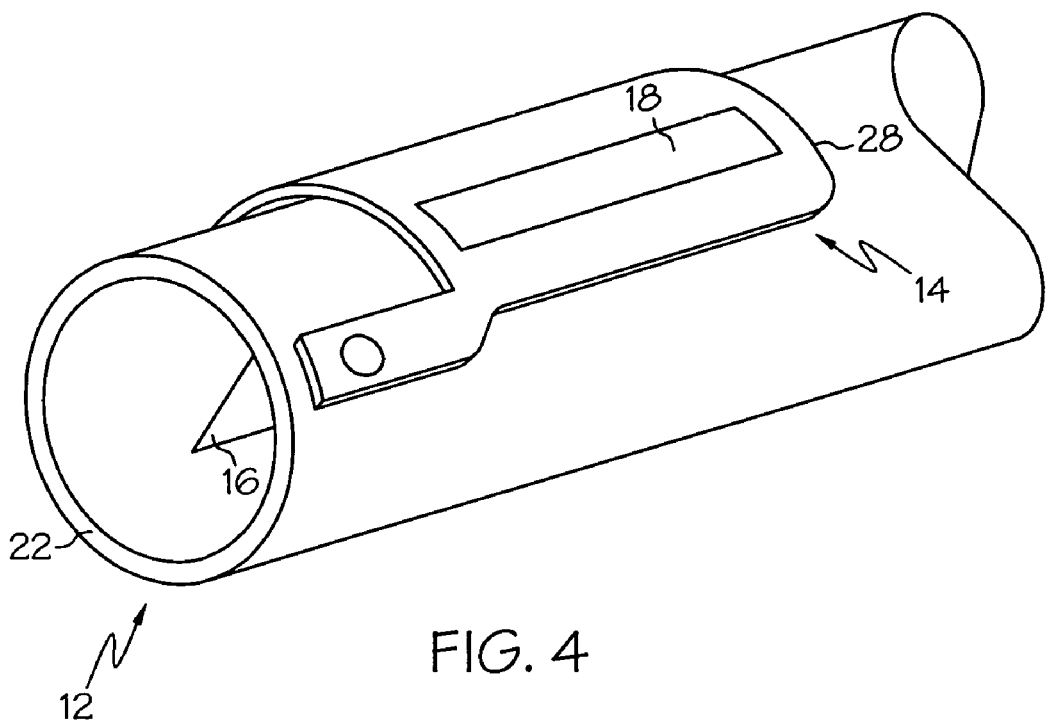
FIG. 4 is a perspective view of the assemblage of FIG. 3, but with the injection needle withdrawn into the distal end of the catheter and with the rotatable member rotated to a second rotational position.

In one application of the embodiment of FIGS. 1-7, in the first rotational position, the rotatable member 14 is substantially aligned with the distal end 22 of the medical catheter 12 and extends distal of the distal end 22 of the medical catheter 12 (as shown in FIGS. 2 and 3). In one variation, the rotatable member 14 has a distal end 28, and the injection needle 16 is movable to extend from the distal end 22 of the catheter 12 and from the distal end 26 of the rotatable member 14 when the rotatable member 14 is in the first rotational position (as shown in FIGS. 2 and 3).

In the same or a different application, in the second rotational position, the rotatable member 14 is substantially aligned with the distal end 22 of the medical catheter 12 and extends proximal of the distal end 22 of the medical catheter 12. In one variation, the injection needle 16 is movable to extend from the distal end 22 of the medical catheter 12 when the rotatable member 14 is in the second rotational position (as can be envisioned from FIG. 4).

Figure 5:
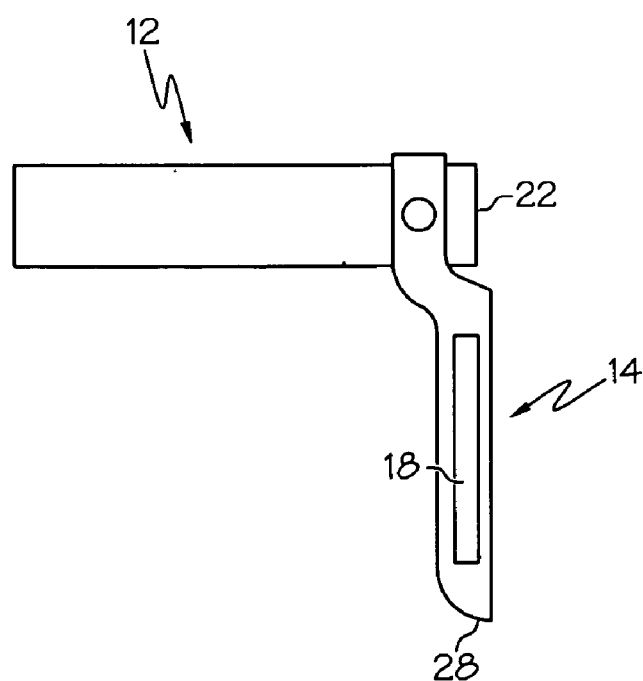
FIG. 5 is a side elevational view of the assemblage of FIG. 4, but with the rotatable member rotated to a third rotational position.

In the same or a different application, the rotatable member 14 has a third rotational position substantially midway between the first and second rotational positions. In one variation, the rotatable member 14 is substantially perpendicular to the medical catheter 12 in the third rotational position (as shown in FIG. 5). It is noted that the rotatable member 14 would block full extension of the injection needle 16 for most rotational positions between the rotational position of FIGS. 2 and 3 and the rotational position of FIG. 5 as can be envisioned by the artisan.

Figure 6:
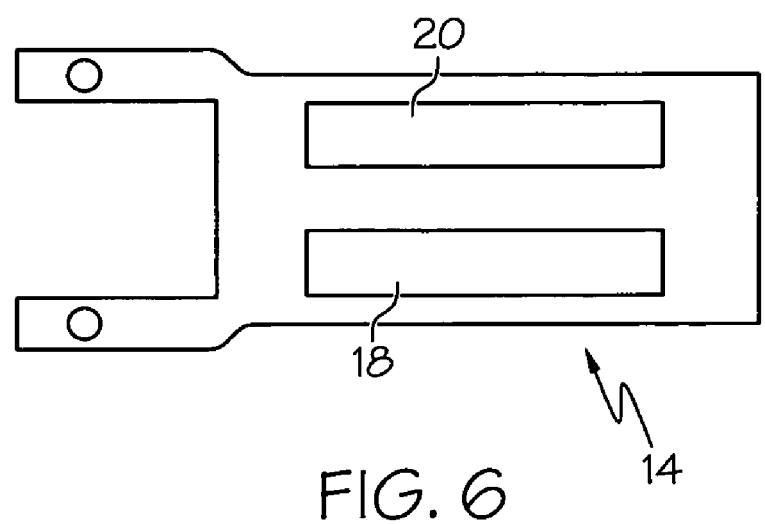
FIG. 6 is a top planar view of a distal end portion of the rotatable member of FIG. 2 showing two medical-treatment electrodes supported by the rotatable member.

In one arrangement of the embodiment of FIGS. 1-7, the at-least-one medical-treatment electrode 18 and 20 includes spaced-apart first and second medical-treatment electrodes 18 and 20 (as seen in FIG. 6). In one employment, the first and second medical-treatment electrodes 18 and 20 are used for bipolar application of medical radio-frequency (RF) energy to patient tissue.

A method for substantially stopping bleeding in patient tissue, using one enablement of the medical instrument 10 of the embodiment of FIGS. 1-7 includes steps a) through e). Step a) includes inserting the distal end 22 of the medical catheter 12 into the working channel opening 24 of an endoscope 26 with the injection needle 16 retracted within the distal end 22 of the medical catheter 12 and with the rotatable member 14 rotated to one of the first and second rotational positions. Step b) includes, after step a), extending the injection needle 16 and delivering a vasoconstrictor drug through the injection needle 16 to the patient tissue. Step c) includes, after step b), retracting the injection needle 16. Step d) includes, after step c), rotating the rotatable member 14 to a rotational position different from the one of the first and second rotational positions. Step e) includes, after step d), medically treating the patient tissue using the first and second medical-treatment electrodes 18 and 20 to substantially stop bleeding in the patient tissue.

In one example of the method of the previous paragraph, steps b) and c) are performed with the rotatable member 14 rotationally disposed at the one of the first and second rotational positions. In another example, steps b) and c) are performed with the rotatable member 14 rotationally disposed at the third rotational position.

Figure 7:
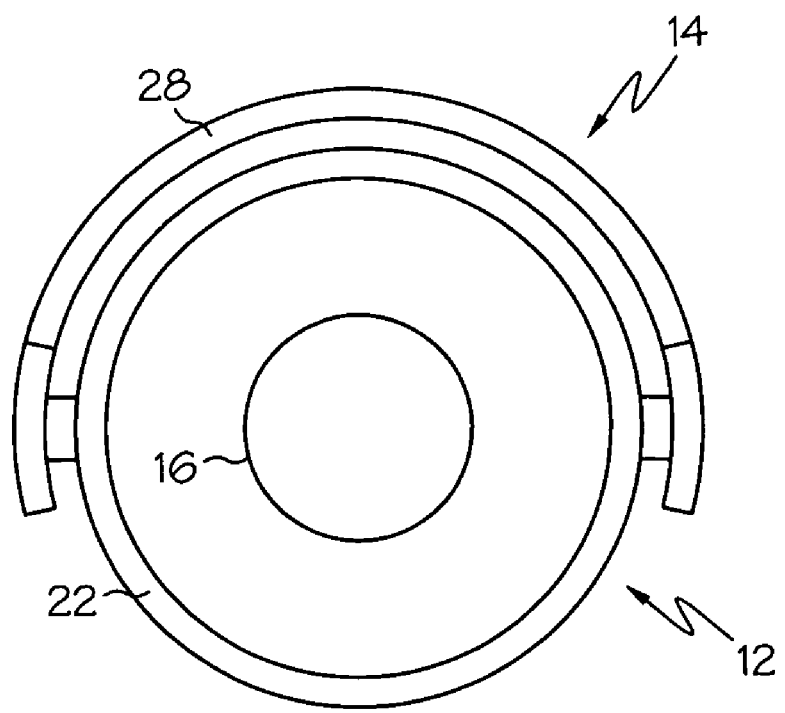
FIG. 7 is a distal end view of the assemblage of FIG. 2, but with the injection needle withdrawn into the distal end of the catheter exposing the lumen in the catheter which is adapted to receive the injection needle.

In one illustration of the embodiment of FIGS. 1-7, the rotatable member 14 has a distal end 28, and, as seen in FIG. 7, the rotatable member 14 has a shape of an annular circular segment having an inner radius when viewed on the distal end 28 of the rotatable member 14. In this illustration, the medical catheter 12 has an outer radius, and the inner radius is substantially equal to the outer radius. In one variation, the rotatable member 14 is substantially transparent. In one modification, the rotatable member 14 is somewhat flexible being made of very thin material but gains some rigidity due to its arcuate shape.

In one construction of the embodiment of FIGS. 1-7, the endoscope 26 is a flexible endoscope and includes an endoscope handpiece 30 and an endoscope flexible tube 32 having a proximal end 34 which is attached to the endoscope handpiece 30 and which is in communication with the working channel opening 24. The endoscope flexible tube 32 has a distal end portion 36 which is insertable into a body passageway of a patient. In one variation, the endoscope 26 includes knobs 38 allowing the user to manipulate the distal end portion 36 of the endoscope flexible tube 32 and includes buttons 40 allowing the user to deliver air or water to the distal end portion 36, to supply suction to the distal end portion 36, to take photo snapshots from the distal end portion 36, etc. In one modification, the endoscope 26 includes monitor cabling 42 shown, in FIG. 1, extending from the endoscope handpiece 30 to a monitor (not shown). Typically, a "lens cap" (not shown) covers the working channel opening 24 when the opening is not in use. Examples of endoscopes include, without limitation, gastroscopes and colonoscopes.

In the same or a different construction, the medical catheter 12 and the rotatable member 14 are flexible and each comprise, consist essentially of, or consist of polyethylene, polyurethane, or polyester. In one variation, the at-least-one medical-treatment electrode 18 and 20 is bonded to a transparent polyester substrate (not shown) which is bonded to the rotatable member 14, and a lead (not shown) is bonded to the at-least-one medical-treatment electrode 18 and 20. In one example, a cable 44 operatively connects a medical radio-frequency (RF) generator 45 to the lead for the at-least-one medical-treatment electrode 18 and 20 in the handle 46 of the medical instrument 10. A first tube 48 is operatively connected to the handle 46 and is connectable to a source of saline solution (not shown), and a second tube 50 is operatively connected to the handle 46 and leads to a source of vasoconstrictor drug (not shown). Control levers, pull knobs, etc., of the medical instrument 10, to rotate the rotatable member 14, to extend and retract the injection needle 16, to control the flow of saline solution in a passageway (not shown) of the medical catheter 12 to irrigate patient tissue, and to control the flow of vasoconstrictor drug through the injection needle 16 have been omitted for clarity. Mechanisms able to rotate a rotatable member 14 and mechanisms able to extend and retract an injection needle 16 are within the ordinary level of skill of those knowledgeable about endoscopes and other medical instruments.

Figure 8:
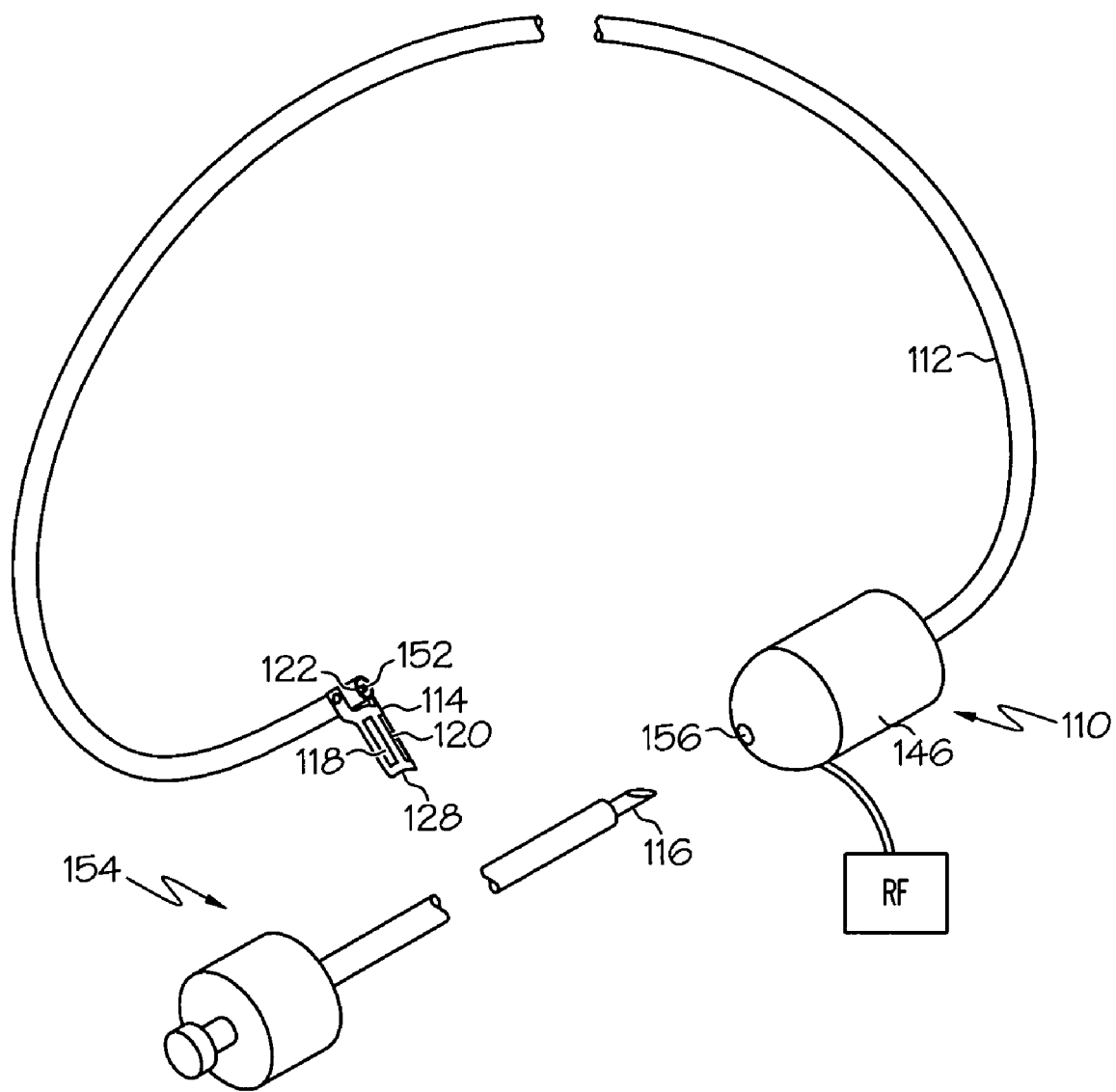
FIG. 8 is a schematic, perspective view of a second embodiment of a medical instrument of the invention and a medical radio-frequency (RF) generator which, in one employment, is used with the medical instrument.

A second embodiment of a medical instrument 110 of the invention is shown in FIG. 8 and is basically the same as the medical instrument 10 of the embodiment of FIGS. 1-7 except that instead of describing the medical instrument as including the injection needle, the medical instrument is described as having a lumen adapted to receive an injection needle. This allows, in one example, for the injection needle to be part of a medical device which is a separate device from the medical instrument but which interacts with, and operates through, the medical instrument.

More specifically, the medical instrument 110 of the embodiment of FIG. 8 includes a medical catheter 112, a rotatable member 114, and at least one medical-treatment electrode 118 and 120. The medical catheter 112 has a distal end 122 and has a lumen 152 adapted to receive an injection needle 116 movable in the lumen 152 to extend from, and to retract within, the distal end 122 of the medical catheter 112. The rotatable member 114 is connected to the medical catheter 112 proximate the distal end 122 of the medical catheter 112 and is rotatable with respect to the medical catheter 112 between a first rotational position and a second rotational position. The at-least-one medical-treatment electrode 118 and 120 is supported by the rotatable member 114.

In one enablement of the embodiment of FIG. 8, the distal end 122 of the medical catheter 112 is insertable into a working channel opening of an endoscope (not shown). In another enablement, the distal end 122 of the medical catheter 112 is insertable into a channel (not shown) on the outside of the flexible tube of the endoscope or is attachable to a ring (not shown) on the outside of the distal end portion of the endoscope. In another enablement, the distal end 122 of the medical catheter 112 is insertable into a channel of a steerable medical device (not shown). Other enablements (including the use of the medical catheter 112 without channel or ring assistance) are left to the artisan.

In one application of the embodiment of FIG. 8, in the first rotational position, the rotatable member 114 is substantially aligned with the distal end 122 of the medical catheter 112 and extends distal of the distal end 122 of the medical catheter 112. In one variation, the rotatable member 114 has a distal end 128, and the injection needle 116 is part of an injection-needle device 154. In this variation, the medical instrument 110 also includes a handle 146 having an injection-needle port 156 in communication with the lumen 152, and the injection needle 116 is manually insertable into the injection-needle port 156 and manually movable in the lumen 152 to extend from the distal end 122 of the medical catheter 112 and from the distal end 128 of the rotatable member 114 when the rotatable member 114 is in the first rotational position.

In the same or a different application, in the second rotational position, the rotatable member 114 is substantially aligned with the distal end 122 of the medical catheter 112 and extends proximal of the distal end 122 of the medical catheter 112. In one variation, The injection needle 116 is part of an injection-needle device 154. In this variation, the medical instrument 110 also includes a handle 146 having an injection-needle port 156 in communication with the lumen 152, and the injection needle 116 is manually insertable into the injection-needle port 156 and manually movable in the lumen 152 to extend from the distal end 122 of the medical catheter 112 when the rotatable member 114 is in the second rotational position.

In the same or a different application, the rotatable member 114 has a third rotational position substantially midway between the first and second rotational positions. In one variation, the rotatable member 114 is substantially perpendicular to the medical catheter 112 in the third rotational position (as shown in FIG. 8).

In one arrangement of the embodiment of FIG. 8, the at-least-one medical-treatment electrode 118 and 120 includes spaced-apart first and second medical-treatment electrodes 118 and 120. In one employment, the first and second medical-treatment electrodes 118 and 120 are used for bipolar application of medical radio-frequency (RF) energy to patient tissue.

A method for substantially stopping bleeding in patient tissue, using one enablement of the medical instrument 110 of the embodiment of FIG. 8 includes steps a) through e). Step a) includes inserting the distal end 122 of the medical catheter 112 into the working channel opening of an endoscope (such as working channel opening 24 of endoscope 26) with the rotatable member 114 rotated to one of the first and second rotational positions. Step b) includes, after step a), manually inserting the injection needle 116 into the injection-needle port 156 of the handle 146 of the medical instrument 10, manually moving the injection needle 116 in the lumen 152 of the medical catheter 112, and delivering a vasoconstrictor drug through the injection needle 116 to the patient tissue. Step c) includes, after step b), manually retracting the injection needle 116. Step d) includes, after step c), rotating the rotatable member 114 to a rotational position different from the one of the first and second rotational positions. Step e) includes, after step d), medically treating the patient tissue using the at-least-one medical-treatment electrode 118 and 120 to substantially stop bleeding in the patient tissue.

In one example of the method of the previous paragraph, steps b) and c) are performed with the rotatable member 114 rotationally disposed at the one of the first and second rotational positions. In another example, steps b) and c) are performed with the rotatable member 114 rotationally disposed at the third rotational position.

In one illustration of the embodiment of FIG. 8, the rotatable member 114 has a distal end 128, and the rotatable member 114 has a shape of an annular circular segment having an inner radius when viewed on the distal end 128 of the rotatable member 114. In this illustration, the medical catheter 112 has an outer radius, and the inner radius is substantially equal to the outer radius. In one variation, the rotatable member 114 is substantially transparent. In one modification, the rotatable member 114 is somewhat flexible being made of very thin material but gains some rigidity due to its arcuate shape.

In one application of the first and/or second embodiment, the at-least-one medical-treatment electrode is flexible providing yet more intimate contact between the electrode and patient tissue which reduces charring of patient tissue and which improves non-visual monitoring of tissue treatment. In one variation, wherein the rotatable member is transparent, a video camera (not shown) of the endoscope is used to visually monitor the medical treatment of the patient tissue between the first and second medical-treatment electrodes.

In one procedure employing an example of the first and/or second embodiment, the flexible tube of the endoscope is inserted into the esophagus of a patient to have a few cellular layers of patient tissue be medically treated by the at-lest-one medical-treatment electrode. It is noted that when the at-least-one medical-treatment electrode consists of a single electrode, the single electrode would be operated in a monopolar manner as is known to the artisan. When the at-least-one medical-treatment electrode consists of two or more electrodes, the electrodes many be operated in a monopolar or a dipolar manner as is known to those skilled in the art.

Several benefits and advantages are obtained from one or more of the embodiments of the invention. In one application, having a rotatable member support the at-least-one medical-treatment electrode allows the medical catheter to be inserted into, and withdrawn from, the esophagus (or other body lumen) of a patient with the rotatable member rotated to extend straight out or straight back (retroflexed) from the distal end of the medical catheter and allows the rotatable member to rotate to an advantageous rotational position to provide more intimate contact between the at-least-one medical-treatment electrode and patient esophageal (or other) tissue for improved hemostasis.

While the present invention has been illustrated by a description of several embodiments and examples, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical instrument comprising:
   a) a medical catheter having a distal end;
   b) a rotatable member hingedly connected to the medical catheter proximate the distal end of the medical catheter and rotatable with respect to the medical catheter between a first rotational position and a second rotational position, wherein in the first rotational position the rotatable member is coaxially aligned with the distal end of the medical catheter and extends distal of the distal end of the medical catheter, and wherein in the second rotational position the rotatable member is coaxially aligned with the distal end of the medical catheter and extends proximal of the distal end of the medical catheter;
   c) an injection needle movable to extend from, and to retract within, the distal end of the medical catheter for at least one of the first and second rotational positions of the rotatable member; and
   d) at least one medical-treatment electrode supported by the rotatable member.

2. The medical instrument of claim 1, wherein the rotatable member has a distal end, and wherein the injection needle is movable to extend from the distal end of the medical catheter and from the distal end of the rotatable member when the rotatable member is in the first rotational position.

3. The medical instrument of claim 1, wherein the rotatable member has a distal end, and wherein the injection needle is movable to extend from the distal end of the medical catheter when the rotatable member is in the second rotational position.

4. The medical instrument of claim 1, wherein the rotatable member has a third rotational position substantially midway between the first and second rotational positions.

5. The medical instrument of claim 1, wherein the at-least-one medical-treatment electrode includes spaced-apart first and second medical-treatment electrodes.

6. A method for substantially stopping bleeding in patient tissue, using a medical instrument, wherein the medical instrument includes: a medical catheter having a distal end; a rotatable member connected to the medical catheter proximate the distal end of the medical catheter and rotatable with respect to the medical catheter between a first rotational position and a second rotational position; an injection needle movable to extend from, and to retract within, the distal end of the medical catheter for at least one of the first and second rotational positions of the rotatable member; and at least one medical-treatment electrode supported by the rotatable member, wherein the at-least-one medical-treatment electrode includes spaced-apart first and second medical-treatment electrodes, and wherein the method comprises the steps of:
   a) inserting the distal end of the medical catheter into the working channel opening of an endoscope with the injection needle retracted within the distal end of the medical catheter and with the rotatable member rotated to one of the first and second rotational positions;
   b) after step a), extending the injection needle and delivering a vasoconstrictor drug through the injection needle to the patient tissue;
   c) after step b), retracting the injection needle;
   d) after step c), rotating the rotatable member to a rotational position different from the one of the first and second rotational positions; and
   e) after step d), medically treating the patient tissue using the first and second medical-treatment electrodes to substantially stop bleeding in the patient tissue.

7. The medical instrument of claim 1, wherein the rotatable member has a distal end, and wherein the rotatable member has a shape of an annular circular segment having an inner radius when viewed on the distal end of the rotatable member, wherein the medical catheter has an outer radius, and wherein the inner radius is substantially equal to the outer radius.

8. The medical instrument of claim 7, wherein the rotatable member is substantially transparent.

9. A medical instrument comprising:
   a) a medical catheter having a distal end and having a lumen adapted to receive an injection needle movable in the lumen to extend from, and to retract within, the distal end of the medical catheter;
   b) a rotatable member hingedly connected to the medical catheter proximate the distal end of the medical catheter and rotatable with respect to the medical catheter between a first rotational position and a second rotational position, wherein in the first rotational position the rotatable member is coaxially aligned with the distal end of the medical catheter and extends distal of the distal end of the medical catheter, and wherein in the second rotational position the rotatable member is coaxially aligned with the distal end of the medical catheter and extends proximal of the distal end of the medical catheter; and
   c) at least one medical-treatment electrode supported by the rotatable member.

10. The medical instrument of claim 9, wherein the rotatable member has a distal end, and wherein the injection needle is part of an injection-needle device, wherein the medical instrument also includes a handle having an injection-needle port in communication with the lumen, and wherein the injection needle is manually insertable into the injection-needle port and manually movable in the lumen to extend from the distal end of the medical catheter and from the distal end of the rotatable member when the rotatable member is in the first rotational position.

11. The medical instrument of claim 9, wherein the rotatable member has a distal end, and wherein the injection needle is part of an injection-needle device, wherein the medical instrument also includes a handle having an injection-needle port in communication with the lumen, and wherein the injection needle is manually insertable into the injection-needle port and manually movable in the lumen to extend from the distal end of the medical catheter when the rotatable member is in the second rotational position.

12. The medical instrument of claim 9, wherein the rotatable member has a third rotational position substantially midway between the first and second rotational positions.

13. The medical instrument of claim 9, wherein the at-least-one medical-treatment electrode includes spaced-apart first and second medical-treatment electrodes.

14. A method for substantially stopping bleeding in patient tissue, using a medical instrument including: a medical catheter having a distal end and having a lumen adapted to receive an injection needle movable in the lumen to extend from, and to retract within, the distal end of the medical catheter; a rotatable member connected to the medical catheter proximate the distal end of the medical catheter and rotatable with respect to the medical catheter between a first rotational position and a second rotational position; and at least one medical-treatment electrode supported by the rotatable member, wherein in the first rotational position the rotatable member is substantially aligned with the distal end of the medical catheter and extends distal of the distal end of the medical catheter, wherein the rotatable member has a distal end, wherein the injection needle is part of an injection-needle device, wherein the medical instrument also includes a handle having an injection-needle port in communication with the lumen, wherein the injection needle is manually insertable into the injection-needle port and manually movable in the lumen to extend from the distal end of the medical catheter and from the distal end of the rotatable member when the rotatable member is in the first rotational position, and wherein the method comprises the steps of:
 a) inserting the distal end of the medical catheter into the working channel opening of an endoscope with the rotatable member rotated to one of the first and second rotational positions;
 b) after step a), manually inserting the injection needle into the injection-needle port of the handle of the medical catheter, manually moving the injection needle in the lumen of the medical catheter, and delivering a vasoconstrictor drug through the injection needle to the patient tissue;
 c) after step b), manually retracting the injection needle;
 d) after step c), rotating the rotatable member to a rotational position different from the one of the first and second rotational positions; and
 e) after step d), medically treating the patient tissue using the at-least-one medical-treatment electrode to substantially stop bleeding in the patient tissue.

15. A medical instrument comprising:
 a) a medical catheter having a distal end and having a lumen adapted to receive an injection needle movable in the lumen to extend from, and to retract within, the distal end of the medical catheter;
 b) a rotatable member hingedly connected to the medical catheter proximate the distal end of the medical catheter and rotatable with respect to the medical catheter between a first rotational position and a second rotational position, wherein in the first rotational position the rotatable member is coaxially aligned with the distal end of the medical catheter and extends distal of the distal end of the medical catheter, and wherein in the second rotational position the rotatable member is coaxially aligned with the distal end of the medical catheter and extends proximal of the distal end of the medical catheter; and
 c) at least one medical-treatment electrode supported by the rotatable member; wherein the rotatable member has a distal end, and wherein the rotatable member has a shape of an annular circular segment having an inner radius when viewed on the distal end of the rotatable member, where the medical catheter has an outer radius, and wherein the inner radius is substantially equal to the outer radius.

16. The medical instrument of claim 15, wherein the rotatable member is substantially transparent.

\* \* \* \* \*